US006221857B1

(12) United States Patent
Vandenbergh et al.

(10) Patent No.: US 6,221,857 B1
(45) Date of Patent: Apr. 24, 2001

(54) ALTERING SEX RATIO OF OFFSPRING IN MAMMALS

(75) Inventors: John G. Vandenbergh, Raleigh; Jacob A. Konzelmann, Charlotte; Andrew K. Hotchkiss, Cary, all of NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/095,222

(22) Filed: Jun. 10, 1998

(51) Int. Cl.[7] .................................................. A61K 31/56

(52) U.S. Cl. ........................... 514/169; 514/178; 514/182

(58) Field of Search ..................................... 514/169, 178, 514/182

(56) References Cited

U.S. PATENT DOCUMENTS 4,001,403    1/1977    Bennett et al. ...................... 424/184

FOREIGN PATENT DOCUMENTS

WO88/00827    2/1988    (WO) .

OTHER PUBLICATIONS

Clarke et al., "Hormonally mediated inheritnace of acquired characteristic in mongolian gerbils", Nature, vol. 364, p. 712, 1993.*

Clarke et al., "A gerbil dam's fetal intrauterine position affects the sex ratios of litters she gestates", Physiology & Behavior, vol. 57, pp. 297–299, 1995.*

Vandenbergh et al., "Mother's prior intrauterine position affects the sex ratio of her offspring in house mice", Proc. Natl. Acad. Sci., USA, vol. 91, pp. 11055–11059, 1994.*

Austad et al;/;Sex–ratio manipulation in the common opossum; Nature, 324:58–60 (1986).

Bondrup–Nielsen; Emigration of meadow voles, Microtus pennsylvanicus: the effect of sex ratio; Oikos, 65:2:358–360 (1992).

Carter et al.; Neonatal Androgen and Adult Sexual Behavior in the Golden Hamster; Physiology & Behavior, 9:89–95 (1972).

Clark et al.; Concentrations of Sex Steroid Hormones in Pregnant and Fetal Mongolian Gerbils; Physiology & Behavior, 49:239–243 (1990).

Clark et al.; Hormonally mediated inheritance of acquired characteristics in Mongolian gerbils; Nature 364:712 (1993).

Clark et al.; Androgen Mediated Effects of Male Fetuses on the Behavior of Dams Late In Pregnancy; Developmental Psychobiology, 26(1)23–35 (1993).

Clark et al.; A Gerbil Dam's Fetal Intrauterine Position Affects the Sex Ratios of Litters She Gestates, Physiology& Behavior, 57:297–299 (1995).

Crews et al., Role of reductase and aromatase in sex determination in the red–eared slider (Trachemys script), a turtle with temperature–dependendent sex determination, Journal of Endocrinology, 143:279–289 (1994).

Davis et al.; reduced Ratio of Male to Female Births in Several Industrial Countries, JAMA,279;1018–1023 (1998).

Edwards et al.; Early Androgen Treatment and Male and Female Sexual Behavior in Mice, Hormones& Behavior, 2:49–58 (1971).

Gill et al.; Acute Prenatal Androgen Treatment Increases Birth Weights and Growth Rates in Lambs, Journal of Animal Science,73:2600–2608 (1995).

Gledhill; Selection and Separation of X–and Y–Chromosome–Bearing Mammalian Sperm, Gamete Research, 20:377–396 (1988).

Guerrero; Association of the Type and the Time of Insemination within the Menstrual Cycle with the Human Sex Ratio at Birth, The New England Journal of Medicine, 291:1056–1059 (1974).

Harlap; Gender of Infants Conceived on Different Days of the Menstrual Cycle, The New England Journal of Medicine, 300:1445–1448 (1979).

Hedricks et al.; Timing of Insemination Is Correlated With the Secondary Sex Ratio of Norway Rats; Physiology& Behavior,48:625–632 (1990).

Hornig et al.; Unmasking sex–ratio biasing through targeted analysis, Animal Behavior;47:1224–1226 (1994).

Houtsmuller et al.; Plasma Testosterone in Fetal Rats and Their Mothers on Day 19 of Gestation Physiology& Behavior,57:495–499 (1995).

Huck et al.; Litter sex ratios in the golden hamster vary with time of mating and litter size and are not binomially distributed, Behaviorial Ecology and Sociobiology,26:99–109 (1990).

Huck et al.; Food Restricting Young Hamsters (Mesocricetus auratus) Affects Sex Ratio and Growth of Subsequent Offspring, Biology of Reproduction,35:592–598 (1986).

James, The Hypothesized Hormonal Control of Mammalian Sex Ratio at Birth–A Second Update, J. Theoretical Biology, 155:121–128 (1992).

James, Testosterone Levels, Handedness and Sex Ratio, J. Theoretical Biology,133:261–266 (1988).

James, Hormonal Control of sex Ratio, J. Theoretical Biology,118:427–441 (1986).

(List continued on next page.)

Primary Examiner—Barbara P. Badio
(74) Attorney, Agent, or Firm—Myers Bigel Sibley & Sajovec

(57) ABSTRACT

Methods of altering sex ratios in mammalian populations by treating pregnant female mammals (P generation) with hormones or anti-hormones are described. The sex ratio of the F1 generation born to treated mammals exhibits a normal sex ratio, but the sex ratio of the F2 generation is altered depending on the active agent given to the pregnant dam. Administration of androgens to the P generation dam results in an F2 generation with more males than would be expected in the absence of treatment; administration of an anti-androgen results in more females.

33 Claims, No Drawings

OTHER PUBLICATIONS

James, Parental Hormone Levels and Mammalian Sex Ratios at Birth, *J. Theoretical Biology*, 139:59–67 (1989).

James, The Hypothesized Hormonal Control of Human Sex Ratio at Birth–an Update, *J. Theoretical Biology*, 143:555–564 (1990).

James, Sex Ratios of the Offspring of Patients with Multiple Sclerosis, *Neuroepidemiology*, 13:216–219, (1994).

James, The Human Sex Ratio, Part 2: A Hypothesis and a Program of Research, *Human Biology*, 59:873–900 (1987).

McClure, Sex–Biased Litter Reduction in Food–Restricted Wood Rats, *Science*, 2111058–1060 (1981).

Meikle et al.; Food availability and secondary sex ratio variation in wild and laboratory house mice, *J. Reprod Fert.*, 78:587–591 (1986).

Meikle et al.; Maternal dominance rank and secondary sex ratio in domestic swine, *Animal Behavior*, 46:79–85 (1993).

Nichols et al.; The effect of a single dose of testosterone propionate on activity, and natal dispersal in the meadow vole, Microtus pennsylvanicus, *Annales Zoological Fennici*, 32:209–215 (1995).

Reiling et al.; Effect of Prenatal Androgenization on Performance, Lactation, Carcass, and Sensory Traits of Heifers in a Single–Calf Heifer System, *Journal of Animal Science*, 73:986–992 (1995).

Rhind et al.; Effect of Passive Immunization Against Testosterone on the Reproductive Performance of Scottish Blackface Ewes in Different Levels of Body Condition at Mating, *Animal Production*, 41:97–102 (1985).

Rines et al.; Fetal Effects on sexual Behavior and Aggression in Young and Old Female Mice Treated with Estrogen and Testosterone, *Hormones and Behavior*, 18:117–129 (1984).

Vandenbergh et al.; Mother's prior intrauterine position affects the sex ratio of her offspring in house mice; *Proc. Natl. Acad. Sci. USA*, 91:11055–11059 (1994).

Vandenbergh et al.; The Anogenital Distance Index, a Predictor of the Intrauterine Position Effects on Reproduction in Female House Mice; *Laboratory Animal Science*, 45:567–573 (1995).

Vom Saal, Sexual Differentiation in Litter–Bearing Mammals: Influence of Sex of Adjacent Fetuses in Utero, *Journal of Animal Science*, 67:1824–1840 (1989).

Vom Saal et al.; Sexual Characteristics of Adult Female Mice Are Correlated with Their Blood testosterone Levels During Prenatal Development, *Science*, 209:5597–599 (1980).

Zielinski et al.; The effect of intrauterine position on the survival, reproduction and home range size of female house mice, *Behav Ecol Sociobiol*, 30:185–191 (1992).

Zielinski et al.; Effect of Intrauterine Position and Social Density on Age of First Reproduction in Wild–Type Female House Mice, *Journal of Comparative Psychcology*, 105:134–139 (1991).

Zielinski et al.; Effects of Social Stress and Intrauterine Position on Sexual Phenotype in Wild–Type House Mice, *Physiology& Behavior*, 49:117–123 (1991).

* cited by examiner

ALTERING SEX RATIO OF OFFSPRING IN MAMMALS

FIELD OF THE INVENTION

The present invention relates to methods of altering sex ratios in mammalian populations by treating pregnant female mammals (P generation) with hormones or anti-hormones. The sex ratio of the F1 generation born to treated mammals exhibits a normal sex ratio, but the sex ratio of the F2 generation is altered depending on the active agent given to the pregnant dam. Administration of androgens to the P generation dam results in an P2 generation with more males than would be expected in the absence of treatment; administration of an anti-androgen results in more females.

BACKGROUND OF THE INVENTION

The expected sex ratio for a given population of mammals is approximately 50% males. Attempts to alter this ratio by genetic selection in mice and fruit flies have been unsuccessful (see, e.g., Falconer, *Am. Nat.* 88:385 (1954); Laurie, *Proc. R. Soc. London* 133:248 (1946)). However, alterations of the sex ratio have been described in several wild and laboratory populations of mammals. Sex ratio alterations have been ascribed to a number of environmental factors including food supply (see, e.g., Austad and Sunquist, *Nature* 324:58 (1986); McClure, *Science* 211:1058 (1981); Meikle and Drickamer, *J. Repro. Fert.* 78:587 (1986)); timing of mating (see, e.g., Hendricks and McClintock, *Physiol. Behav.* 48:625 (1990); Horning and McClintock, *Anim. Behav.* 47:1224 (1994); Huck et al., *Behav. Ecol. Sociobiol.* 26:99 (1990)); social dominance status (see, e.g., Meikle et al., *Anim. Behav.* 46:79 (1993)); and intrauterine position of the fetus (see, e.g., Clark et al., *Nature* 364:712 (1993); Vandenbergh and Huggett, *PNAS* (*USA*) 91:11055 (1994); Clark and Galef, *Physiol. Behav.* 57:297 (1995)).

Further, some alterations in sex ratio have been made in domestic farm animals by taking advantage of differential characteristics of the Y- and X-bearing sperm. To date, no controlled physiological manipulation of the pregnant female has been reported to alter sex ratio in naturally conceived mammalian populations.

SUMMARY OF THE INVENTION

A first aspect of the present invention is a method of treating a pregnant mammal to alter the sex ratio of the F2 generation. The pregnant mammal (P generation) is treated with an active agent with hormonal effects, with the active agent being administered to the P generation dam prior to the end of sexual differentiation of F1 female embryos. An F1 female is allowed to mature and mated, and the resulting F2 generation exhibits an altered sex ratio (more males or more females, depending on the active agent administered) than would expected in the absence of said treatment.

A further aspect of the present invention is a method of treating a pregnant mammal with an androgen, to increase the ratio of males in the F2 generation. The pregnant mammal (P generation) is treated with an androgen, the androgen being administered to the P generation dam prior to the end of sexual differentiation of F1 female embryos. An F1 female is allowed to mature and mated, and the resulting F2 generation contains more males than would expected in the absence of said treatment.

A further aspect of the present invention is a method of treating a pregnant mammal with an anti-androgen, to increase the ratio of females in the F2 generation. The pregnant mammal (P generation) is treated with an anti-androgen, the anti-androgen being administered to the P generation dam prior to the end of sexual differentiation of F1 female embryos. An F1 female is allowed to mature and mated, and the resulting F2 generation contains more females than would expected in the absence of said treatment.

A further aspect of the present invention is a method of treating a pregnant mammal with an estrogen, to increase the ratio of females in the F2 generation. The pregnant mammal (P generation) is treated with an estrogen, the estrogen being administered to the P generation dam prior to the end of sexual differentiation of F1 female embryos. An F1 female is allowed to mature and mated, and the resulting F2 generation contains more females than would expected in the absence of said treatment.

DETAILED DESCRIPTION OF THE INVENTION

Four mechanisms have been proposed to result in alteration of sex ratios: asynchronous breeding, sperm selection, sex specific embryonic mortality, and concentration of gonadotropins and gonadal steroids at conception. Asynchronous breeding relates to the time of insemination relative to the stage of the estrus cycle.

Females who are fertilized near the time of ovulation produce more females than those who are fertilized either before or after ovulation. Sperm selection operates either by favoring the survival or fertilizing ability of either the X- or Y-bearing sperm. Sex-specific embryonic mortality may occur by favoring the survival of one gonotype over another; this may result from differences in male and female responses to sub-optimal gestational conditions. James (*J. Theor. Biol.* 143:555 (1990)) theorized that, in humans, parental hormone levels at the time of conception affect the sex of offspring, with high levels of gonadotropin favoring production of males and high levels of androgen or estrogen favoring the production of females. However, only correlational evidence is available to support this theory. Similarly, no physiological mechanism(s) have been experimentally confirmed as underlying any of the above mechanisms of sex ratio alteration.

The intrauterine position (IUP) of a female rodent has been shown to influence the sex ratio of litters produced by that rodent. Clark et al., *Nature* 364:712 (1993); Vandenbergh and Huggett, *PNAS* (*USA*) 91:11055 (1994); Clark and Galef, *Physiol. Behav.* 57:297 (1995). Vandenbergh and Huggett (*PNAS* (*USA*) 91:11055 (1994)) reported that female mice gestated between two males produced 61.2% males; females gestated with one male adjacent produced 52.9% males; and females gestated without adjacent males produced 42.4% males. In addition to altering sex ratio, intrauterine position has been reported to masculinize the anatomy, physiology and behavior of offspring (vom Saal, *J. Animal Sci.* 67:1824 (1989)). The sex of the immediate neighbors of a developing fetus determines the relative testosterone exposure of that fetus in utero (Clark et al., *Physiol. Behav.* 49:239 (1991)). The more males adjacent to a female fetus, the higher the testosterone exposure and the greater the degree of masculinization.

The present inventors have determined that hormonal active agents administered to pregnant female mice results in an alteration (from the expected 50:50 ratio) of sex ratio in the subsequent F2 generation. Where the hormone administered to the parental dam is an androgen, the F1 daughters produce male-biased litters. Where an anti-androgen is administered to the parental dam, the F1 daughters produce female-biased litters.

While not wishing to be held to a particular theory of action, the present inventors believe that hormonal changes occurring in utero preset developing females to subsequently produce litters biased toward a specific sex. The altered sex ratios in litters may result from the preferential loss of zygotes of a particular sex. Alternatively, females exposed to hormones in utero may engage in breeding that is asynchronous with the estrous cycle.

Asynchronous breeding may occur due to physiological changes (irregular estrous cycles) or to behavioral effects (mating behavior asynchronous with estrous). Previous studies have reported that animals exposed in utero to elevated physiological levels of testosterone exhibit increased occurrence of abnormal estrus cycles (vom Saal, *J. Anim. Aci.* 67:1824 (1989); Hotchkiss and Vandenbergh, unpublished data). Differences in female mating behavior due to prenatal endocrine exposure have also been documented (Rines and vom Saal, *Horm. Behav.* 18:117 (1984)), and might lead to significant discrepancy between coitus and endocrine status of the female.

The present inventors have determined that hormones or antihormones administered to pregnant female (P generation) mammals result in the production of offspring (F1 generation) with the expected approximately 50:50 sex ratio, but that the F1 daughters produce offspring (F2) with altered sex ratios. The treatment of the F1 females while in utero presets the developing females to subsequently produce offspring biased toward a certain sex.

As used herein, a method of altering sex ratio refers to a treatment that results in a statistically significant increase in the percentage of one sex in a generation, compared to the percentage of that sex that would be expected in the absence of treatment. The present methods affect the sex ratio at the population level, and thus the sex of any particular offspring can be predicted but cannot be assured. Stated another way, the present methods increase the odds that the offspring obtained from a daughter of a treated female will be of a certain sex. The alteration in sex ratio may be measured within litters (for animals with multiple births) or at the population or generation level (for animals with single or multiple births).

In a method of the present invention, developing fetuses are exposed to increased levels of androgens during a preselected period of development, compared to the exposure that would occur in the absence of treatment. This may be accomplished by increasing the androgen level in a pregnant mammal (P) during a preselected period of the pregnancy. Androgen may be administered to the pregnant dam by any suitable means. Such treatment of a pregnant female mammal according to the present invention results in the production of daughters (F1) who produce offspring (F2) having a higher than average proportion of male offspring.

In a further method of the present invention, developing fetuses are exposed to decreased levels of androgen during a preselected period of development, compared to the exposure that would occur in the absence of treatment. The fetal exposure to androgen may be decreased by the administration of androgen blockers or other anti-androgens to the pregnant mammal (P) during a preselected period. Suitable anti-androgens include androgen blockers or androgen receptor antagonists. Such treatment of a pregnant mammal according to the present invention results in the production of daughters (F1) who produce offspring (F2) with a higher than average proportion of female offspring.

In a further method of the present invention, developing fetuses are exposed to increased levels of estrogen during a preselected period of development (compared to exposure that would occur in the absence of treatment). The fetal exposure to estrogen may be increased by administering estrogen to a pregnant mammal (P) during a preselected period of the pregnancy. Increases in estrogen levels may be achieved by any suitable process, including administration of an androgen that is converted to estrogen, or administration of an estrogen (such as estradiol benzoate). Such treatment of a pregnant mammal results in production of daughters (F1) who produce offspring (F2) with a higher than average proportion of female offspring.

In a further method of the present invention, developing fetuses are exposed to decreased levels of estrogen during a preselected period of development (compared to exposure that would occur in the absence of treatment). The fetal exposure to estrogen may be decreased by administering an anti-estrogen to a pregnant mammal (P) during a preselected period of the pregnancy. Anti-estrogens include estrogen blockers such as tamoxifen and EM-652 (Martel et al., *J. Steroid. Biochem. Mol. Biol.* 64:199 (1998). Such treatment of a pregnant mammal results in production of daughters (F1) who produce offspring (F2) with a higher than average proportion of male offspring.

In a further method of the present invention, hormonally active agents are administered to pregnant F1 females produced by the methods described above. The agent administered to the F1 dam is of the same class (e.g., androgen, estrogen, anti-androgen, anti-estrogen) as that administered to the P generation dam, however, the precise dose or method of administration need not be identical across the generations. The treatment of the F1 generation pregnant females increases the sex bias effect seen in the F2 generation (compared to the sex ratio that would occur in the absence of treatment of the F1 female).

In a further method of the present invention, F2 females are obtained from F1 generation dams treated according to any of the above methods and are bred to produce an F3 litter with an altered sex ratio (compared to the sex ratio which would be expected in the absence of any treatment, i.e., in the wild). Pregnant F2 females may optionally be treated with an active agent of the same class as was used to treat the F1 and/or the P generation dams.

F2 or F3 females obtained by any of the above-described methods may be bred repeatedly to produce multiple litters or offspring; hormonally active agents may be administered according to the present methods during any such pregnancy of the F2 and F3 dams to further alter the sex ratio of the resulting offspring.

Active Agents

The androgens are steroids that develop and maintain primary and secondary male sex characteristics. Androgens are derivatives of cyclopentanoperhydrophenanthrene. Endogenous androgens are C-19 steroids with a side chain at C-17, and with two angular methyl groups. Testosterone is the primary endogenous androgen. Methyltestosterone is a synthetic derivative of testosterone suitable for oral administration. Androgens suitable for use in methods of the present invention include testosterone, dihydrotestosterone, active metabolites of testosterone, and synthetic derivatives of testosterone such as testosterone propionate and fluoxymesterone.

Anti-androgens block the synthesis or action of androgens. Compounds that inhibit testosterone synthesis include GnRH agonists such as leuprolide or gonadorelin (Goodman and Gilman, *The Pharmacological Basis of Therapeutics*, Ninth Edition, p. 1453 (1996)). Androgen-receptor antagonists inhibit the binding of androgen to its receptor. Various antiandrogens are known in the art, including cyproterone acetate, flutamide (EULEXIN®), nilutamide, and bicalutamide (CASODEX®). See also, U.S. Patent No. U.S. Pat. No. 5,593,981; U.S. Pat. No. 5,610,150; U.S. Pat. No. 4,161,540; U.S. Pat. No. 3,995,060.

Estrogen refers estrogenic hormones and synthetic estrogens that exert the biological effects characteristic of estrogenic hormones. Estrogens are secreted primarily by the ovaries and, in pregnancy, by the placenta. Various different natural forms of estrogen are known, including estradiol, estrone and estriol. Steroidal estrogens include estradiol, estradiol valerate, estradiol cypionate, mestranol, quinestrol, estrone and estrone sulfate. Nonsteroidal compounds with estrogenic activity include diethystilbestrol. Estrogenic compounds from plant sources are known, including coumestrol and genistein.

Anti-estrogens block the synthesis or action of estrogens. Anti-estrogens that block binding of estrogen to its receptor include tamoxifen and clomiphene. Other anti-estrogen agents are known that inhibit the biosynthesis of estrogen.

Formulations suitable for use in the present invention are made according to methods and procedures known in the art.

As used herein, the term "hormones" includes androgens and estrogens. As used herein, an "agent with hormonal activity" includes compounds whose administration alters either the level of hormones existing in a subject animal, or alters the effect of the hormones existing in a subject animal. Agents with hormonal activity include natural and synthetic androgens, natural and synthetic estrogens, anti-androgens, and anti-estrogens. Anti-hormones block the synthesis of a hormone, or block its effects in the body (e.g., by binding to the hormone receptor).

In vertebrate embryos, the gonads appear relatively late in development, after many of the organ systems are well developed. In mammals, male genitalia develops only in the presence of testosterone. For some time during embryonic development of mammals, the embryos remain in a sexually indifferent stage during which the gonadal ridge develops but does not differentiate toward either male or female structures. The appearance of testes initiates masculine sexual differentiation (i.e., the end of the sexually indifferent stage). Testes begin producing testosterone about day 11 in the mouse and this hormone induces the development of the genital tract and masculinization of the brain. In mice and rats, further sexual differentiation continues to about day 5 after parturition.

As used herein, the sexually indifferent stage refers to the period from the development of the gonadal ridge to the presence of clearly differentiated genitalia.

In methods of the present invention, hormones or other active agents are administered to pregnant females prior to the end of sexual differentiation of female embryo(s). The present inventors have determined that artificial administration of agents with hormonal effects to the developing fetus in utero affects the sex ratio of offspring subsequently produced by that female. Additionally, where sexual differentiation of the subject animal is known to continue during the neonatal period, the administration of the active agent may occur during the neonatal period in order to affect the sex ratio of offspring produced by that animal when it matures. Neonatal administration must occur prior to the end of sexual differentiation of the neonate.

In methods of the present invention, the active agents are administered to the pregnant P generation dam. Administration occurs after conception but prior to the end of sexual differentiation of developing female embryo(s) carried by the dam. Administration may occur at any time during pregnancy, but preferably occurs just prior to or at the time of testicular differentiation, or soon thereafter (which time will vary among species as is known in the art). In mice, administration may thus occur during a period at about the midpoint of pregnancy (e.g., during a period calculated to encompass the time of testicular differentiation in mice). A preferred time of administration in murine subjects is about day 11 of pregnancy, or a period of time that encompasses day 11; in different species, a preferred time of administration is that which corresponds embryologically to the preferred murine time of administration (i.e., the embryos of the two species are developmentally similar).

The active agent is administered to the pregnant female in an amount effective to alter the sex ratio of the F2 generation. Where an androgen is administered, it is administered in an amount effective to increase the ratio of males in the F2 generation; where an anti-androgen is administered, it is administered in an amount effective to increase the ratio of females in the F2 generation. In rats, mice and other rodents, a suitable dose of androgen is that which raises the circulating androgen in the pregnant dam to a concentration equal to or greater than that found in female mice gestated between two males in utero (vom Saal, *J. Science* 67:1824 (1989); vom Saal *Science,* 208:597 (1980)). When using testosterone propionate in mice, and adjusting for body size of the pregnant mouse, the dose of testosterone propionate is expected to range from about 0.25 $\mu$g/g BW to about 1.5 $\mu$g/g BW, or even 2.0 $\mu$g/g BW to replicate vom Saal's findings. The upper dose of androgen is limited to doses that do not masculinize the F1 female genitalia such that copulation is negatively affected.

Where the subject animal is a mouse and the active agent is testosterone or testosterone propionate, the active agent is administered at doses of from about 0.5 $\mu$g/g body weight (BW), up to about 0.6 $\mu$g/g BW, 0.7 $\mu$g/g BW, 0.8 $\mu$g/g BW, 0.9 $\mu$g/g BW, 1.0 $\mu$g/g BW, 1.25 $\mu$g/g BW, 1.5 $\mu$g/g BW, or above. Where the subject animal is a mouse and the active agent is flutamide, the dosage may range from about 0.5 mg, 0.75 mg, 1.0 mg, 1.5 mg, 2.0 mg, 2.5 mg, 3.0 mg, 3.5 mg, 4.0 mg, 4.5 mg or 5.0 mg per mouse per day.

Administration of agents with hormonal activity to subjects may occur by any suitable method, including but not limited to by parental administration, implant under the skin, intravenous injection, subcutaneous injection, intraperitoneal injection, oral administration, transdermally, rectally or nasally.

Subjects

The methods of the present invention are useful for altering the sex ratios of mammals, including those of laboratory animals (e.g., rats and mice), livestock (e.g., rabbits, goats, sheep, cows), companion animals (e.g., dogs, cats) and exotics (e.g., zoo animals). In certain cases, the production of more males is desired, such as in the production of laboratory rats. In some livestock species, males exhibit a steeper growth curve early in life and produce leaner meat than females of equivalent age; whereas in others (such as swine), females are leaner than males at time of slaughter in the U.S. Acker and Cunnigham, *Animal Science and Industry*, Prentice Hall, Saddle River, N.J. In other cases, such as in dairy farm livestock, the production of more females is usually preferred. The methods of the present invention are suitable for use in mammals, including porcines, ovines, bovines, rodents, carnivora, primates and non-human primates. The present methods may be used in all female breeding animals, in only those that are mated naturally (i.e., that are not artificially inseminated), or in those that are artificially inseminated. Although the effects of the present methods are more readily apparent in species with multiple births, the methods may also be used in species that routinely give birth to one or two offspring at a time.

The examples which follow are set forth to illustrate the present invention, and are not to be construed as limiting thereof.

EXAMPLE 1

Effect of Testosterone Propionate on F2 Sex Ratio

Charles River CD-1 albino mice were maintained on a 14:10 light/dark cycle and were provided with Prolab 3000 food and water ad lib. Three to four month old females of an intermediate prenatal androgen environment were selected using the anogenital distance (AGD) index. At day 22 of age, females were measured for body weight and AGD. AGD was measured with calipers from the base of the genital papilla to the proximal end of the anal opening. Care was taken to ensure that the skin was not stretched or compressed. The AGD index (AGDI) was calculated as: AGDI= (AGD in mm at weaning)×100/weight in g at weaning. Females of intermediate androgen exposure were then selected as described in Vandenbergh and Huggett, *Lab. Anim. Sci.* 45:567 (1994).

The selected females were mated at three to four months of age with stud males, and the date of the vaginal plug was noted. On day 11 after the vaginal plug was noted, dams were injected subcutaneously every other day from day 11–17 of gestation with either (a) 0.5 μg/g body weight of testosterone propionate (low testosterone treatment); (b) 0.75 μg/g body weight of testosterone propionate (high testosterone treatment); or (c) peanut oil vehicle control. The high dose (0.75 μg/g BW) dose was based on the fetal testosterone measurements of vom Saal (*Science*, 208:597 (1980)). Females were allowed to deliver vaginally. The litter size and sex ratio of the F1 generation was noted on post natal day one and again at weaning on day 22. The AGD Index was measured for F1 females in the control, low testosterone and high testosterone groups. No significant difference in AGDI existed among the groups (data not shown).

F1 generation females were allowed to mature and were mated with stud males. The resulting litters in the F2 generation were counted and sexed at day one and again on day 22.

The observed litter size and sex ratio for the F1 generation did not differ significantly from the untreated controls. Table 1. However, F1 generation females produced litters (F2) with a significant male bias, compared to the vehicle-treated controls. Table 1. Analysis of the data in terms of the proportion of litters that were male-biased revealed that 44% of control litters, 67% of the low testosterone-treated group, and 80% of the litters in the high testosterone-treated group were male biased (p<0.05). (In six litters, four in the control group and two in the low-testosterone treatment group, the sex ratio was 50:50; in these cases an equal number of litters were placed above and below the 50% cut-off.) No differences were noted in litter size and very low pup mortality (2.9%) occurred between day one and 22.

TABLE 1

| P-generation treatment | F1 Generation | | | F2 Generation | | |
|---|---|---|---|---|---|---|
| | # litters | mean litter size | % male ± SE | # litters | mean litter size | % male ± SE |
| Oil control | 7 | 12.7 ± 0.97 | 44.0 ± 4.72 | 34 | 12.2 ± 0.44 | 50.3 ± 2.56 |
| 0.5 μg/g TP | 5 | 12.4 ± 0.55 | 49.7 ± 8.77 | 18 | 11.3 ± 0.68 | 57.9 ± 3.41 |
| 0.75 μg/g TP | 3 | 12.3 ± 1.33 | 48.1 ± 5.87 | 15 | 11.9 ± 0.70 | 60.0 ± 4.44* |

*Significantly different at $P < 0.05$ based on chi-square test.

The mechanism by which the sex ratio was altered in this experiment is as yet unknown but may operate prior to implantation of the blastocyst, either as a result of preferential fertilization by the Y-bearing sperm or preferential implantation of the male blastocyst. Litter size did not differ significantly among the treatment groups, suggesting no differential post-implantation loss. Previous investigations on the factors responsible for alterations in sex ratio have focused on the offspring born to a treated dam. Here we have demonstrated that the effect of in utero hormone exposure "skips a generation" and some mechanism of endocrine memory exists resulting in the production of a disproportionately high number of males by the daughters of testosterone-treated dams.

EXAMPLE 2

Effect of Androgen Antagonist on F2 Sex Ratio

Female mice were selected as described in Example 1, above. The selected females were mated at age seven weeks with stud males, and the date of the vaginal plug was noted. The pregnant mice were treated with flutamide (an androgen antagonist) or control as follows. On day 11 after the vaginal plug was noted, dams were injected subcutaneously every other day from day 11–17 of gestation with either (a) 2.5 mg flutamide per mouse per day (low dose treatment); (b) 3.5 mg flutamide per mouse per day (high dose treatment); or (c) peanut oil vehicle control. Dosages were based on Keisler et al., *Biol. of Reprod.* 44:707 (1991). Females were allowed to deliver vaginally. The litter size and sex ratio of the F1 generation was noted on post natal day one and again at weaning on day 22. The observed litter size and sex ratio for the F1 generation did not differ significantly from the untreated controls. The AGD Index was measured for F1 females in the control, low flutamide and high flutamide groups. No significant difference in AGDI existed among the groups (data not shown).

F1 generation females were allowed to mature and were mated with stud males. The resulting litters in the F2 generation were counted and sexed at day one and again on day 22. The results in the F2 generation are shown in Table 2.

TABLE 2

| Treatment | # of litters | % female | litters with male bias |
|---|---|---|---|
| Control | 9 | 52.0% | 5/9 |
| Low Flutamide | 4 | 56.3% | 1/4 |
| High Flutamide | 4 | 62.0%* | 0/4 |

*Significant at $p < 0.05$

EXAMPLE 3

Dose of Androgen and F2 Sex Ratio

The administration of varied doses of testosterone propionate to pregnant mice is assessed to determine effects on sex ratio of the F2 generation. Female mice are selected and mated as described in Example 1. Testing is conducted as described in Example 1 with dosages of TP ranging from about 1.0 μg/g BW up to and including 8.0 μg/g BW testosterone propionate (and increments in between), and with a vehicle control group. Dams are allowed to deliver vaginally, and the litter size and sex ratio of the F1 generation is noted on post natal day one and again at weaning on day 22. The observed litter sizes and sex ratios for the F1 generation litters are compared to the control group, and among treatment groups. F1 generation females are allowed to mature and are mated with stud males. The resulting litters in the F2 generation are counted and sexed at day one and again on day 22; the observed litter sizes and sex ratios for the F2 generations are compared to the control group, and among treatment groups.

EXAMPLE 4

Time of Administration of Androgen and Effects on F2 Sex Ratio

Administration of testosterone propionate (TP) at different gestational times is carried out to determine the effects of time of administration on the ratio of males in the F2 generation. Female mice are selected and mated as described above (Example 1). TP is administered to the pregnant dam (P generation) from gestational day (GD) 11–19, and also to the newborn F1 mice during the first five postnatal days (PND). The neonatal period is tested because both rats and mice are known to continue to differentiate sexually for about 5 days postpartum. Edwards and Burge, *Horm. Behav.* 2:49 (1971); Carter et al. *Physiol. Behav.* 9:89 (1972). Dams are injected on day 1 and day 3 of the treatment period.

Three groups of ten mice are studied; each group consists of 3–4 month old females of intermediate prenatal androgen exposure (as determined by the AGDI). Testosterone propionate is administered in a dose that results in significant bias of F2 litters toward males, as determined in Example 1 or 3, above. Each group is divided into mice receiving testosterone propionate and mice receiving vehicle control. The groups vary in the time of administration of testosterone propionate: gestational day (GD) 11–14; GD 15–18; and GD 19-postnatal day (PND) 3. See Table 3. Dams are allowed to deliver vaginally, and the litter size and sex ratio of the F1 generation is noted on post natal day one and again at weaning on day 22. The observed litter sizes and sex ratios for the F1 generation are compared to the untreated controls, and among treatment groups. F1 generation females are allowed to mature and are mated with stud males. The resulting litters in the F2 generation are counted and sexed at day one and again on day 22; the observed litter sizes and sex ratios for the F2 generation are compared to those of the untreated controls, and among treatment groups.

TABLE 3

| Group | Treatment | Time of administration |
|---|---|---|
| Group 1 | TP | GD 11–19 |
| | Control | |
| Group 2 | TP | GD 15–18 |
| | Control | |
| Group 3 | TP | GD 19–PND 3 |
| | Control | |

EXAMPLE 5

Dose of Androgen Antagonist and F2 Sex Ratio

Testing as in Example 2 with higher dosages of flutamide, compared to oil control vehicles to determine optimum dose.

The administration of varied doses of flutamide to pregnant mice is assessed to determine effects on sex ratio of the F2 generation. Female mice are selected and mated as described in Example 1. Testing is conducted as described in Example 2 with dosages of flutamide selected from among 2.0, 3.0, 4.0, 5.0 and 6.0 mg of flutamide per mouse per day, and with a vehicle control group. Dams are allowed to deliver vaginally, and the litter size and sex ratio of the F1 generation is noted on post natal day one and again at weaning on day 22. The observed litter sizes and sex ratios for the F1 generation litters are compared to the control group, and among treatment groups. F1 generation females are allowed to mature and are mated with stud males. The resulting litters in the F2 generation are counted and sexed at day one and again on day 22; the observed litter sizes and sex ratios for the F2 generations are compared to the control group, and among treatment groups.

EXAMPLE 6

Time of Administration of Androgen Antagonist and Effects on F2 Sex Ratio

Administration of flutamide to pregnant mice at different gestational times is carried out to determine the effects of time of administration on the ratio of females in the F2 generation. Female mice are selected and mated as described above (Example 1). Flutamide is administered to the pregnant dam (P generation) from gestational day (GD) 11–19, and also to the newborn F1 mice during the first five postnatal days (PND). The neonatal period is tested because both rats and mice are known to continue to differentiate sexually for about 5 days post-partum. Edwards and Burge, *Horm. Behav.* 2:49 (1971); Carter et al. *Physiol. Behav.* 9:89 (1972). Dams are injected on day 1 and day 3 of the treatment period.

Three groups of ten mice are studied; each group consists of 3–4 month old females of intermediate prenatal androgen exposure (as determined by the AGDI). Flutamide is administered in a dose that results in significant bias of F2 litters toward females, as determined in Example 2 or 5, above. Each group is divided into mice receiving flutamide and mice receiving vehicle control. The groups vary in the time of administration of flutamide: gestational day (GD) 11–14; GD 15–18; and GD 19-postnatal day (PND) 3. Table 4. Dams are allowed to deliver vaginally, and the litter size and sex ratio of the F1 generation is noted on post natal day one and again at weaning on day 22. The observed litter sizes and sex ratios for the F1 generation are compared to the untreated controls, and among treatment groups. F1 generation females are allowed to mature and are mated with stud males. The resulting litters in the F2 generation are counted and sexed at day one and again on day 22; the observed litter sizes and sex ratios for the F2 generation are compared to those of the untreated controls, and among treatment groups.

TABLE 4

| Group | Treatment | Time of administration |
|---|---|---|
| Group 1 | Flutamide | GD 11–19 |
| | Control | |
| Group 2 | Flutamide | GD 15–18 |
| | Control | |
| Group 3 | Flutamide | GD 19–PND 3 |
| | Control | |

EXAMPLE 7

Aromatization of Testosterone and Effects on F2 Sex Ratio

Testosterone is converted intracellularly to estrogen (estradiol) in the ovaries and some other hormone-dependent tissues. To study whether the effects of testosterone on sex ratio of F2 litters is due to the presence of estrogen resulting from the aromatization of testosterone, the administration of testosterone (0.75 µg/g BW), estradiol benzoate (EB; 0.075 µg/g BW), dihydrotestosterone (a non- aromatizable androgen; 0.75 µg/g BW), and vehicle control are compared. Parental mice are selected, reared and mated as described above. Timing and dosing protocols are as described in the examples above. The F1 generation is reared, mated, and the resulting F2 generation is assessed for sex ratio, as described above.

EXAMPLE 8

Sex Ratio Effects on F3 Litters

The above examples assess sex ratio bias in the F2 generation produced after hormonal manipulation of the parental generation (P) dam. The present example assesses the effect of hormonal manipulation of the P dam on sex ratio in the F3 generation.

Fifteen F2 dams are randomly selected from the F2 groups described above in which a significant bias toward males was observed in the F2 generation. F2 dams are allowed to mature and are mated as described above. The resulting F3 generation is assessed for male sex ratio bias, as described above.

EXAMPLE 9

Enhancement of Sex Ratio Effects in F2 Generation by Treatment of F1 Generation

The present example tests whether F2 dams (descended from testosterone- treated P dams, in which a significant bias toward males was observed in the F2 generation) may be sensitized to the effect of testosterone, such that administration of testosterone to F1 dams could significantly bias the sex ratio of F2 litters.

Twenty F1 dams are randomly selected from F1 groups (described above) descended from testosterone-treated P dams, in which a significant bias toward males was observed in the F2 generation, and twenty F1 dams are selected from control groups. F1 dams descended from treatment groups are randomized into two groups of ten, one group receiving injections of testosterone and the other receiving vehicle control injections. F1 dams descended from control groups are similarly divided into two groups of ten, one group receiving injections of testosterone and the other receiving vehicle control injections. Testosterone is administered at a time and dose that is demonstrated to have significant sex ratio effects in subsequent litters (see Examples 1, 3 and 4, above). F1 dams are allowed to mature and are mated as described above. The resulting F2 generation is assessed for sex ratio, as described above.

The same test protocol as described above is carried out for F2 dams and the resulting F3 generation is assessed for sex ratio effects, as described above.

EXAMPLE 10

Effects on Subsequent Litters from F2 Dams

Vandenbergh and Huggett reported that second litters born to 2M females (females that were located in utero between two males) had litters significantly biased toward males (*Proc. Natl. Acad. Science* (*USA*) 91:11055 (1994)). To test whether the sex bias effects identified in the above examples continues in subsequent litters, groups of F1, F2 and F3 females with first litters showing significant sex bias (either male or female bias) are re-mated, and the resulting litters are examined for sex bias.

EXAMPLE 11

Investigation of Asynchronous Breeding

Prenatally androgenized female mice have irregular estrous cycles (Hotchkiss and Vandenbergh, unpublished data). Mating before or after the time of ovulation can increase the probability of male offspring (Horning and McClintock, *Animal Behavior* 47:1224 (1994)).

To determine whether the sex bias effects observed in the Examples provided above are due to asynchronous breeding, 20 dams with intermediate AGDI scores are divided into two groups and treated with either a vehicle control or an amount of testosterone known to affect sex ratio in subsequent generations (as established by the Examples described above). These P generation females are allowed to mate and vaginally deliver, as described above. Vaginal smears are then taken from each F1 generation female, for 15 days prior to allowing the F1 female to mate. Monitoring is continued during mating to observe at which point in the estrus cycle vaginal plugs are found. Subsequently, F1 females are monitored for estrus cyclicity on days 21–36 post partum. These studies will determine whether females who exhibit abnormal estrous cycles continue to display abnormal cycles after mating and first pregnancy.

To determine whether asynchronous breeding is occurring due to behavioral effects, treated and control females are placed with a stud male, and vaginal smears are monitored (to determine at what stage of the estrous cycle vaginal plugs appear) and video monitoring is used to observe mating behavior for the first five nights or until a vaginal plug is observed. Behavioral differences to be monitored include (1) the number and duration of mounts; (2) latency to first mount; (3) strength of lordosis; (4) number of fights; (5) length of rostral-rostral proximity; and (6) length of rostral-caudal proximity. Females are inspected at the end of the mating period for a vaginal plug.

EXAMPLE 12

Investigation of Loss of Zygotes

Sixty F1 dams are selected: twenty F1 dams whose hormonal treatment resulted in the production of a high proportion of males in the F2 generation; twenty F1 dams whose hormonal treatment resulted in the production of a low proportion of males in the F2 generation; and twenty control F1 dams that produced a 50:50 sex ratio in the F2 generation. The ovaries and uteri of these females are removed. Ovaries are fixed in 10% buffered formalin, dehydrated, embedded in paraffin, and serially sectioned into 25 micron sections. Representative sections are stained with hematoxylin and eosin and are examined for the number of corpora lutea. Uteri are dissected and microscopically examined for the presence of implantation scars, and scars resulting from successful fetuses are visually differentiated from scars due to reabsorbed fetuses. The number of corpora lutea is compared to the number of implantation sites in each mouse to determine whether zygotic loss occurred. A high degree of zygotic loss among females producing litters with altered sex ratios indicates that sex selection is occurring prior to implantation.

The foregoing examples are illustrative of the present invention, and are not to be construed as limiting thereof. The invention is described by the following claims, with equivalents of the claims to be included therein.

That which is claimed is:

1. A method of treating a pregnant mammal to alter the sex ratio of the F2 generation, comprising:

a) providing a pregnant mammal;

b) administering an active agent with hormonal effects to said pregnant mammal prior to the end of sexual differentiation of F1 female embryos carried by said mammal;

c) allowing an F1 female to mature d) mating said F1 female to produce an F2 generation; wherein the sex ratio of the F2 generation is altered compared to that expected in the absence of said treatment.

2. A method according to claim 1, wherein said active agent is administered to the pregnant mammal during the period of pregnancy in which gonadal differentation of the embryo occurs.

3. A method according to claim 1 wherein said active agent is selected from the group consisting of androgens, anti-androgens, estrogens and anti-estrogens.

4. A method according to claim 1 wherein said active agent is testosterone.

5. A method according to claim 1 wherein administration of said active agent is selected from the group consisting of parenteral administration, subcutaneous administration, intravenous administration, oral administration or transdermal administration.

6. A method according to claim 1 wherein said mammal is a rodent.

7. A method according to claim 1 wherein said mammal is a mouse.

8. A method according to claim 1 wherein said mammal is a rat.

9. A method according to claim 1, further comprising administration of said active agent with hormonal effects to said F1 female during pregnancy, during the period of pregnancy in which gonadal differentiation of the embryo occurs.

10. A method of treating a pregnant mammal to increase male offspring in the F2 generation, comprising:
 a) providing a pregnant mammal;
 b) administering an androgen to said pregnant mammal prior to the end of sexual differentiation of F1 female embryos carried by said mammal;
 c) allowing an F1 female to mature
 d) mating said F1 female to produce an F2 generation; wherein the sex ratio of said F2 generation contains more males compared to that expected in the absence of said treatment.

11. A method according to claim 10 wherein said androgen is administered to the pregnant mammal during the period of pregnancy in which gonadal differentiation of the embryo occurs.

12. A method according to claim 10 wherein said androgen is testosterone.

13. A method according to claim 10 wherein administration of said androgen is selected from the group consisting of parenteral administration, subcutaneous administration, intravenous administration, oral administration or transdermal administration.

14. A method according to claim 10 wherein said mammal is a rodent.

15. A method according to claim 10 wherein said mammal is a mouse.

16. A method according to claim 10 wherein said mammal is a rat.

17. A method according to claim 10, further comprising administration of an androgen to said F1 female during pregnancy, during the period of pregnancy in which gonadal differentiation of the embryo occurs.

18. A method of treating a pregnant mammal to increase female offspring in the F2 generation, comprising:
 a) providing a pregnant mammal;
 b) administering an anti-androgen to said pregnant mammal prior to the end of sexual differentiation of F1 female embryos carried by said mammal;
 c) allowing an F1 female to mature
 d) mating said F1 female to produce an F2 generation; wherein the sex ratio of said F2 generation contains more females compared to that expected in the absence of said treatment.

19. A method according to claim 18 wherein said anti-androgen is administered to the pregnant mammal during the period of pregnancy in which gonadal differentiation of the embryo occurs.

20. A method according to claim 18 wherein said anti-androgen is selected from the group consisting of agents that inhibit androgen synthesis and androgen-receptor antagonists.

21. A method according to claim 18 wherein said anti-androgen is flutamide.

22. A method according to claim 18 wherein administration of said anti-androgen is selected from the group consisting of parenteral administration, subcutaneous administration, intravenous administration, oral administration or transdermal administration.

23. A method according to claim 18 wherein said mammal is a rodent.

24. A method according to claim 18 wherein said mammal is a mouse.

25. A method according to claim 18 wherein said mammal is a rat.

26. A method according to claim 18, further comprising administration of an anti-androgen to said F1 female during pregnancy, during the period of pregnancy in which gonadal differentiation of the embryo occurs.

27. A method of treating a pregnant mammal to increase female offspring in the F2 generation, comprising:
 a) providing a pregnant mammal;
 b) administering an estrogen to said pregnant mammal prior to the end of sexual differentiation of F1 female embryos carried by said mammal;
 c) allowing an F1 female to mature
 d) mating said F1 female to produce an F2 generation; wherein the sex ratio of said F2 generation contains more females compared to that expected in the absence of said treatment.

28. A method according to claim 27 wherein said estrogen is administered to the pregnant mammal during the period of pregnancy in which gonadal differentiation of the embryo occurs.

29. A method according to claim 27 wherein administration of said estrogen is selected from the group consisting of parenteral administration, subcutaneous administration, intravenous administration, oral administration or transdermal administration.

30. A method according to claim 27 wherein said mammal is a rodent.

31. A method according to claim 27 wherein said mammal is a mouse.

32. A method according to claim 27 wherein said mammal is a rat.

33. A method according to claim 27, further comprising administration of an estrogen to said F1 female during pregnancy, during the period of pregnancy in which gonadal differentiation of the embryo occurs.

* * * * *